(12) United States Patent
Lampe et al.

(10) Patent No.: US 11,234,896 B2
(45) Date of Patent: Feb. 1, 2022

(54) METHOD FOR MONITORING AND IMPROVING FORWARD BLOOD FLOW DURING CPR

(71) Applicant: The Trustees of the University of Pennsylvania, Philadelphia, PA (US)

(72) Inventors: Joshua Lampe, Jenkintown, PA (US); Lance Becker, Philadelphia, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 512 days.

(21) Appl. No.: 14/436,250

(22) PCT Filed: Oct. 17, 2013

(86) PCT No.: PCT/US2013/065416
§ 371 (c)(1),
(2) Date: Apr. 16, 2015

(87) PCT Pub. No.: WO2014/062911
PCT Pub. Date: Apr. 24, 2014

(65) Prior Publication Data
US 2015/0283027 A1    Oct. 8, 2015

Related U.S. Application Data

(60) Provisional application No. 61/714,978, filed on Oct. 17, 2012.

(51) Int. Cl.
*A61H 31/00* (2006.01)
*A61B 5/02* (2006.01)
(Continued)

(52) U.S. Cl.
CPC ......... *A61H 31/005* (2013.01); *A61B 5/026* (2013.01); *A61B 5/0215* (2013.01);
(Continued)

(58) Field of Classification Search
CPC ... A61B 5/026; A61M 1/1087; A61M 1/1096; A61M 1/12; A61M 1/122; A61M 1/125; A61M 2205/3334
See application file for complete search history.

(56) References Cited

U.S. PATENT DOCUMENTS 6,471,656 B1    10/2002    Shalman et al.
2002/0069878 A1 *  6/2002  Lurie ................... A61H 31/005
                                                128/204.18
(Continued)

OTHER PUBLICATIONS

International Preliminary report on Patentability issued in related International Application No. PCT/US2013/065416, dated June 9, 2015.
International Search Report and Written Opinion issued in related International Application No. PCT/US2013/065416, dated April 7, 2014.

*Primary Examiner* — Puya Agahi
(74) *Attorney, Agent, or Firm* — BakerHostetler

(57) ABSTRACT

Devices and methods for blood flow enhancement and hemodynamic power monitoring are provided. A blood flow enhancement device includes a pump system configured to be coupled to a central vasculature of a subject during cardiopulmonary resuscitation (CPR). The pump system includes a pumping mechanism configured to increase forward blood flow generated during the CPR while substantially limiting backward blood flow generated during the CPR. The pumping mechanism being operated concurrently with the CPR. The hemodynamic power monitor is configured to control a chest compression device and an active valve.

10 Claims, 13 Drawing Sheets

(51) Int. Cl.

| | |
|---|---|
| *A61B 5/0215* | (2006.01) |
| *A61M 60/50* | (2021.01) |
| *A61M 60/892* | (2021.01) |
| *A61B 5/026* | (2006.01) |
| *A61N 7/00* | (2006.01) |
| *A61M 60/40* | (2021.01) |
| *A61M 60/122* | (2021.01) |
| *A61M 60/135* | (2021.01) |
| *A61M 60/148* | (2021.01) |
| *A61M 60/205* | (2021.01) |
| *A61M 60/274* | (2021.01) |
| *A61M 60/414* | (2021.01) |
| *A61M 60/894* | (2021.01) |

(52) U.S. Cl.
CPC ...... *A61B 5/02028* (2013.01); *A61B 5/02158* (2013.01); *A61M 60/50* (2021.01); *A61M 60/892* (2021.01); *A61N 7/00* (2013.01); *A61H 31/006* (2013.01); *A61H 2230/04* (2013.01); *A61H 2230/255* (2013.01); *A61H 2230/305* (2013.01); *A61M 60/122* (2021.01); *A61M 60/135* (2021.01); *A61M 60/148* (2021.01); *A61M 60/205* (2021.01); *A61M 60/274* (2021.01); *A61M 60/40* (2021.01); *A61M 60/414* (2021.01); *A61M 60/894* (2021.01); *A61M 2205/3334* (2013.01); *A61M 2205/3358* (2013.01)

(56) References Cited

U.S. PATENT DOCUMENTS

| | | | |
|---|---|---|---|
| 2003/0062040 A1* | 4/2003 | Lurie | A61M 16/20 128/203.11 |
| 2006/0047205 A1 | 3/2006 | Ludomirsky et al. | |
| 2006/0241745 A1* | 10/2006 | Solem | A61F 2/2418 623/2.18 |
| 2007/0142923 A1* | 6/2007 | Ayre | A61M 1/1086 623/31 |
| 2009/0099498 A1* | 4/2009 | Demers | A61M 1/106 604/6.09 |
| 2010/0016731 A1 | 1/2010 | Eggers et al. | |
| 2010/0081912 A1 | 4/2010 | McKenna et al. | |
| 2010/0312123 A1* | 12/2010 | Phillips | A61B 5/021 600/485 |
| 2012/0010543 A1* | 1/2012 | Johnson | A61N 1/3925 601/41 |
| 2012/0165853 A1* | 6/2012 | Paulussen | A61B 5/14546 606/191 |
| 2012/0203147 A1* | 8/2012 | Lurie | A61K 31/21 601/41 |
| 2012/0203158 A1* | 8/2012 | Beyersdorf | A61M 1/3666 604/4.01 |
| 2012/0289869 A1* | 11/2012 | Tyler | A61N 7/00 601/2 |
| 2012/0310037 A1* | 12/2012 | Choi | A61N 1/3987 600/17 |
| 2014/0073973 A1* | 3/2014 | Sexton | A61M 5/1723 600/490 |

* cited by examiner

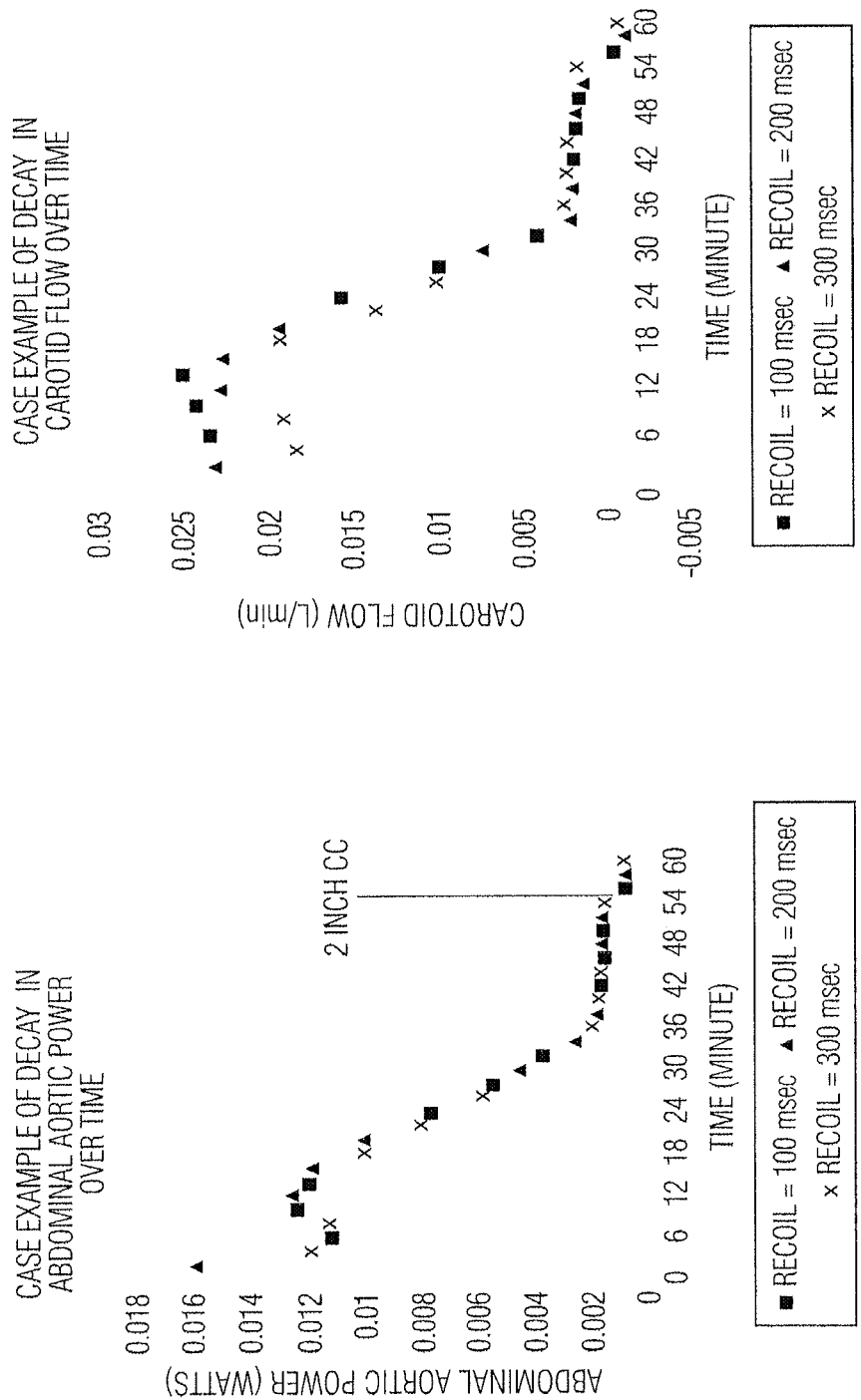

METHOD FOR MONITORING AND IMPROVING FORWARD BLOOD FLOW DURING CPR

CROSS REFERENCE TO RELATED APPLICATIONS

The present application is a National Phase Application of PCT International application No. PCT/US2013/065416 filed Oct. 17, 2013, which claims the benefit of priority from U.S. provisional application No. 61/714,978 filed Oct. 17, 2012 the contents of which are incorporated herein by reference.

STATEMENT REGARDING FEDERALLY SPONSORED RESEARCH

This invention was made with government support under grant number HL067630 awarded by the National Institutes of Health. The government has certain rights in the invention.

FIELD OF THE INVENTION

The present invention relates to cardiopulmonary resuscitation (CPR). More particularly, the present invention relates to methods and devices for increasing forward blood flow during CPR, and to methods and systems for monitoring hemodynamic power.

BACKGROUND OF THE INVENTION

Cardiac arrest relates to the cessation of normal circulation of the blood due to failure of the heart to contract effectively. Cardiac arrest may be due to a variety of circumstances, such as heart disease or significant trauma. Arrested blood circulation may prevent delivery of oxygen to the body. Cardiac arrest is a medical emergency that, in certain situations, is potentially reversible if treated early.

One common treatment for cardiac arrest is an external chest compression technique known as cardiopulmonary resuscitation (CPR). With CPR, repetitive compression of the chest and intermittent positive pressure ventilation is provided to the subject. When the chest is compressed and allowed to recoil, blood circulates to the heart and brain. When a breath is delivered to the subject, the lungs fill with oxygen. Typically, CPR is used to circulate oxygenated blood, and to keep the brain alive until advanced care to restore spontaneous blood circulation can be initiated.

SUMMARY OF THE INVENTION

The present invention also relates to hemodynamic power monitoring systems and methods. The hemodynamic power monitoring system includes a measurement device configured to be positioned in a blood vessel of a subject and a power estimation system. The measurement device is configured to measure a blood flow and a blood pressure in the blood vessel. The power estimation system is coupled to the measurement device. The power estimation system is configured to determine a hemodynamic power based on the measured blood flow and the measured blood pressure. The measurement device measures the blood flow based on a measurement technique selected from the group consisting of a pressure gradient, a Doppler shift, a bristle flow, anemometry, thermodilution, a pitot technique, and an electromagnetic flow.

The present invention also relates to blood flow enhancement devices and methods including a valving system. A blood flow enhancement device includes a valving system including at least one element configured to be coupled invasively or non-invasively to a central vasculature of a subject during CPR. The at least one element is configured to substantially reduce blood flow in at least one blood vessel of the central vasculature. The at least one element is configured to increase forward blood flow generated during the CPR in the central vasculature without substantially reducing the forward blood flow through a brain of the subject.

The present invention relates to blood flow enhancement devices and methods including a pump system. A blood flow enhancement device includes a pump system configured to be coupled to a central vasculature of a subject during CPR. The pump system includes a pumping mechanism configured to increase forward blood flow generated during the CPR while substantially limiting backward blood flow generated during the CPR. The pumping mechanism being operated concurrently with the CPR.

BRIEF DESCRIPTION OF THE DRAWINGS

The invention may be understood from the following detailed description when read in connection with the accompanying drawings. It is emphasized that, according to common practice, various features/elements of the drawings may not be drawn to scale. On the contrary, the dimensions of the various features/elements may be arbitrarily expanded or reduced for clarity. Moreover, in the drawings, common numerical references are used to represent like features/elements. Included in the drawings are the following figures:

FIGS. 9C, 9D, 9E, 10A and 10B are graphs that are useful for describing effects of chest compression release speed on CPR efficiency.

DETAILED DESCRIPTION OF THE INVENTION

Figure 1A:
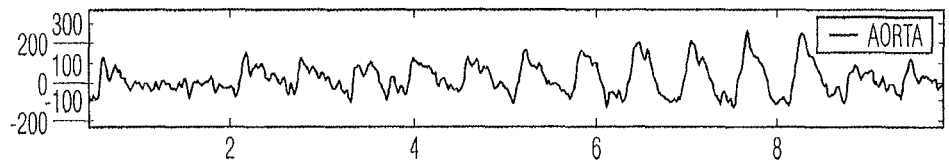
FIGS. 1A, 1B, 1C, 1D, 1E and 1F are example graphs of blood flow as a function of time in several arteries and veins during CPR, illustrating a behavior of a cardiovascular system during CPR.
Figure 1B:
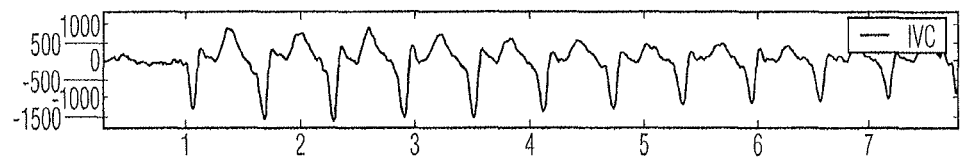
Figure 1C:
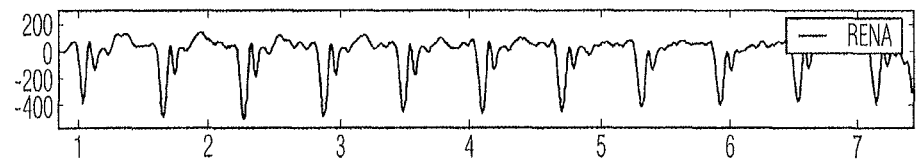
Figure 1D:
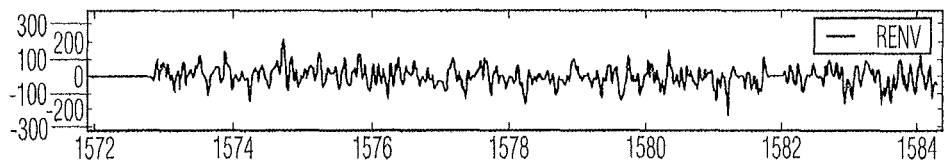
Figure 1E:
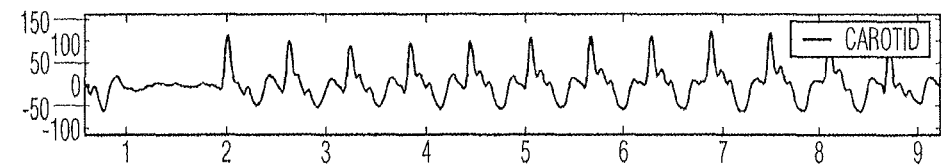
Figure 1F:
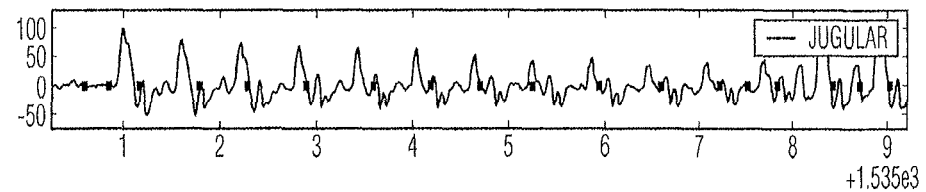

During normal cardiac rhythm, there is typically very little backward flow of blood into the heart, because of the presence of arterial valves which may prevent such backflow. With cardiac arrest, however, the heart fails to contract effectively. Thus, during application of conventional CPR, blood is pumped by increasing the intra-thoracic pressure through the application of a chest compression. In this case, the physiological valves near the heart may be of little value in enforcing forward flow.

For these reasons, conventional CPR may be inefficient with respect to forward blood flow. During CPR, blood moves in forward and reverse directions during chest compressions. This is in contrast to the exclusively forward flow during normal heart function. Thus, blood flow created during CPR may undergo a sloshing effect, with poor (i.e., relatively little) forward blood flow. The sloshing effect may result in ineffective resuscitation attempts when the blood is unable to flow through the lungs and other critical organ systems like the heart and the brain, reducing tissue substrate, i.e., oxygen, delivery and waste, i.e., carbon dioxide, removal required for normal physiology.

Referring to FIGS. 1A-1F, example graphs of blood flow as a function of time during CPR are shown. In particular, FIGS. 1A-1F illustrate example blood flow for the aorta, vena cava, the renal artery, the renal vein, the carotid artery and the jugular vein, respectively. As shown in FIGS. 1A-1F, blood flow travels in both directions, represented by positive and negative flows. This means that CPR may induce blood sloshing more than it may induce forward flow.

It may be appreciated that chest compressions could generate significant blood flow if proper directionality is enforced (i.e., where arteries take blood away from the heart and veins take blood back to the heart). Aspects of the present invention relate to methods and blood flow enhancement devices for improving forward flow during CPR. Aspects of the present invention also relate to improving forward flow while limiting reverse flow during CPR. Methods and blood flow enhancement devices of the present invention may, thus, provide increased re-oxygenation of the blood, which may result in improved survival for cardiac arrest patients. Exemplary blood flow enhancement devices may be used during resuscitation and may be applied to any subject undergoing hemodynamic instability, including, but not limited to, cardiac arrest and other forms of shock, and physiologic states where hemodynamic function is compromised such as congestive heart failure and heart valve regurgitation.

According to an exemplary embodiment, a blood flow device may include a pump system which may be coupled to a central vasculature of a subject during CPR. The central vasculature includes but is not limited to the cervical, brachial, thoracic, abdominal and femoral vasculature. The pump system may include a pumping mechanism to impose a direction of forward blood flow generated during CPR. For example, a high volume saline infusion from an infusion pump may be used to improve the directionality of blood flow.

According to another exemplary embodiment, the blood flow device may include a valving system coupled to the central vasculature during CPR. The valving system may include at least one element to substantially reduce blood flow in at least one blood vessel during CPR. The element may be configured to increase forward blood flow generated during CPR in the central vasculature without substantially reducing the forward blood flow through the subject's brain.

For example, the at least one element may include one or more intravascular valves. The intravascular valves may be inserted into the vessels at the physiologic entrance and exit of the central vasculature, thus creating a large forward flowing pump. Placement of properly directioned one-way valves in the central vasculature may prevent the sloshing that is observed during CPR. According to an exemplary embodiment, the valves may be placed in the abdominal aorta and the carotid artery in the neck to allow the blood to leave the thorax, but not return, and valves may be placed in the jugular vein and vena cava to allow blood to enter the thorax, but not leave. The valving system may isolate the venous vessels from the flow and pressure generated by the compression phase of a chest compression while also isolating the arterial vessels from the flow and pressure generated by the release phase of a chest compression, and may take advantage of the relatively large flow in the proper direction in each vessel while mitigating the flow in the wrong direction.

Aspects of the present invention also relate to methods and systems for quantifying the actual improvement to CPR efficiency, by monitoring hemodynamic power in at least one blood vessel. According to an exemplary embodiment, a hemodynamic power monitoring system may include a measurement device configured to measure blood flow and blood pressure in a blood vessel and a hemodynamic power estimator. The hemodynamic power estimator may determine a hemodynamic power based on the blood flow and the blood pressure.

Figure 2:
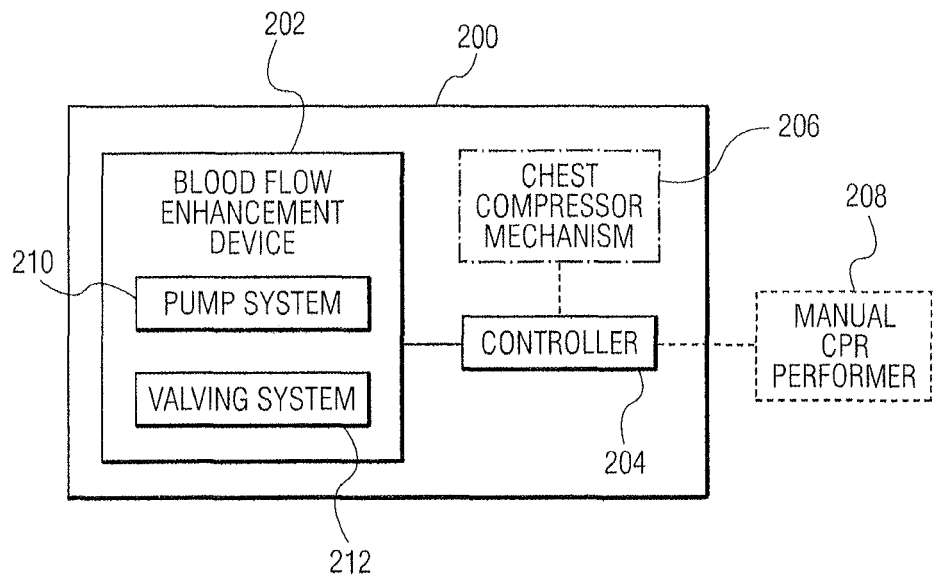
FIG. 2 is a functional block diagram of an exemplary CPR device for increasing forward blood flow during CPR, according to an embodiment of the present invention.

Referring next to FIG. 2, a functional block diagram of CPR device 200 (also referred to herein as device 200) is shown. Device 200 may include blood flow enhancement device 202 and controller 204. Device 200 may optionally include chest compressor mechanism 206. Device 200 may also, optionally, be used by manual CPR performer 208.

Blood flow enhancement device 202 may increase forward blood flow (and may also limit reverse flow) during CPR. Blood flow enhancement device 202 may include pump system 210 and/or valving system 212. Pump system 210 may increase the forward blood flow in the central vasculature. Valving system 212 may include at least one element to substantially reduce blood flow in at least one blood vessel, to control the forward blood flow through the central vasculature.

CPR may be considered to represent an alternating current (AC) flow generating mechanism. In general, blood flow enhancement device 202 may impose a forward directionality on the CPR-induced AC flow, thus improving an efficacy of the CPR. Pump system 210 may superimpose a secondary forward (direct current (DC)) flow (such as via a saline solution or an artery-vein blood infusion) over the chest compression (AC) blood flow. Valving system 212 may impose a forward directionality by acting as a diode, allowing forward blood flow via one or more elements (such as physical or virtual valves), such that the blood flow may proceed in the forward direction. Pump system 210 and valving system 212 are described further below in respective FIGS. 3 and 4.

Controller 204 may be coupled to one or more of blood flow enhancement device 202, chest compressor mechanism 206 and manual CPR performer 208, to control operation and/or adjustment of blood flow enhancement device 202 (and, optionally, chest compressor mechanism 206) during CPR. Controller 204 may include, for example, a logic circuit, a digital signal processor or a microprocessor. Controller 204 may also include one or more memory chips, such as flash memory, for storing data from blood flow enhancement device 202 (and, optionally, chest compressor mechanism 206). Controller 204 may also include a user interface, such as a pointing device, a keyboard and/or a display device for operating device 200.

In some embodiments, device 200 may include chest compressor mechanism 206, which may automatically perform CPR compressions. The valving system 212 of blood flow enhancement device 202 may operate synchronously with chest compressor mechanism 206, via controller 204. Chest compressor mechanism 206 may include any suitable mechanism configured to perform compression (and decompression), for increasing cardiopulmonary circulation during CPR. For example, chest compressor mechanism 206 may decompress the chest and/or compress and decompress the abdomen or other body parts (e.g., lower limbs) in a constant, repetitive manner relative to the chest.

A suitable blood flow enhancement device 202, controller 204 and chest compressor mechanism 206 may be understood by the skilled person from the description herein.

Although the present invention is described above with respect to cardiac arrest, it is understood that methods and devices of the present invention may be applied to any hemodynamic instability (e.g., hemorrhagic shock, septic shock and cardiac arrest) in which the cardiovascular system begins to transition from a DC flow system to an AC flow system (i.e., where blood ceases from flowing exclusively in the proper direction).

Figure 3:
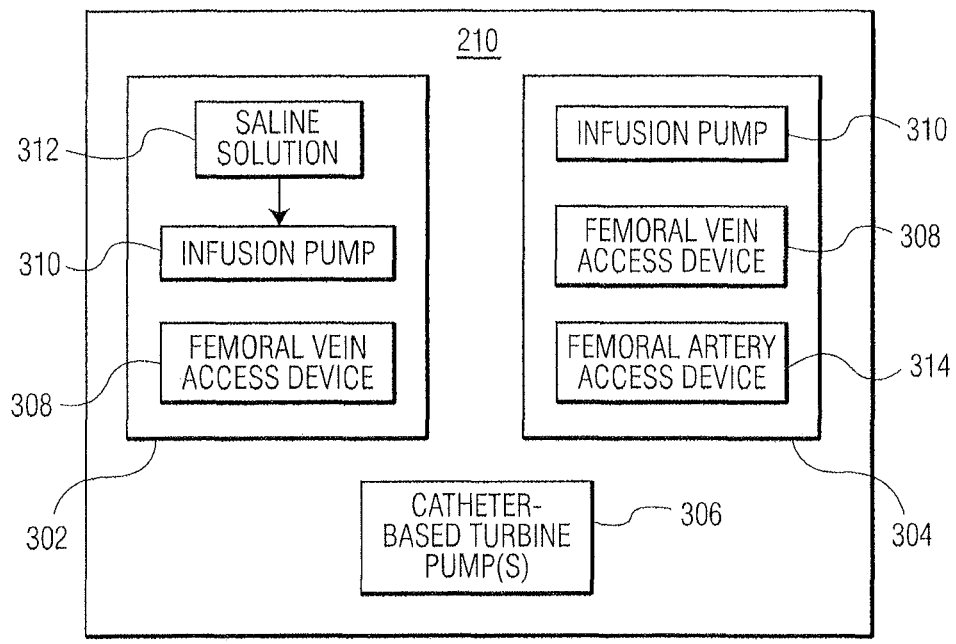
FIG. 3 is a functional block diagram of an exemplary pump system of the CPR device shown in FIG. 2, according to an embodiment of the present invention.

Referring next to FIG. 3, a functional block diagram of pump system 210 is shown. Pump system 210 may include one or more of fluid infusion system 302, blood infusion system 304 and at least one catheter-based turbine impeller pump 306, for example, an Impella® pump (also referred to herein as turbine pump(s) 306 or pump(s) 306). Each of fluid infusion system 302, blood infusion system 304 and pump(s) 306 may be configured to superimpose proper directional flow on forward blood flow (generated by chest compression) during the administration of CPR. Thus, pump system 210 may be operated concurrently with CPR administration.

Fluid infusion system 302 may include femoral vein access device 308, infusion pump 310 and saline solution 312. Femoral access by infusion pump 310 may be established via femoral vein access device 308. Saline solution 312 may be introduced to infusion pump 310. Infusion pump 310 may operate to impose a flow (via saline solution 312) during CPR (which may be administered by hand (via manual CPR performer 208 (FIG. 2) or via chest compressor mechanism 206). In an exemplary embodiment, infusion pump 310 and saline solution 312 are connected to an introducer, and infusion pump 310 is initiated at a delivery rate. In general, the delivery rate of the high volume infusion may be between about 1-6 L/hour. In an exemplary embodiment, the delivery rate is about 4 L/hour.

Fluid infusion system 302 may provide a high volume infusion of saline solution 312 into the femoral vein during CPR. Fluid infusion system 302 may improve forward blood flow by imposing a secondary flow from the legs toward the heart onto the CPR generated blood flow.

According to experimental results (obtained from an animal model), a difference may be observed in the end tidal $CO_2$ ($EtCO_2$). In normal animals, the measured $EtCO_2$ values falls below 10 mmHg after about 20 minutes of CPR. In animals that receive the high volume infusion, the $EtCO_2$ is in the range of about 28-32 mmHg. For reference, normal $EtCO_2$ measurements are typically in the range of about 38-42 mmHg. This difference in $EtCO_2$ as shown by this data and the data in example 5 below, suggests that more blood is flowing through the lungs in those animals that receive the infusion, which may be caused by improved net forward blood flow.

Blood infusion system 304 may include femoral vein access device 308, infusion pump 310 and femoral artery access device 310. Unlike fluid infusion system 302, blood infusion system 304 may not include saline solution 312. Femoral venous and femoral arterial access points may be established via respective femoral vein access device 308 and femoral artery access device 314. Infusion pump 310 may operate to pull blood from the artery and return it to the vein during CPR (which may be administered by hand (via manual CPR performer 208 (FIG. 2) or via chest compressor mechanism 206). In an exemplary embodiment, infusion pump may pump the blood at a rate of about 4 L/hour, to improve venous return during CPR.

Pump(s) 306 may be placed near at least one of the entrances or the exits of the thoracic cavity to generate DC blood flow. Pressure drops across pump(s) 306 may be enforced to drive the forward blood flow in the proper direction. Pump(s) 306 may be mechanically and surgically placed using catheters. For example, pumps 306 may be positioned in the vena cava to drive blood toward the heart, and in the aorta to drive blood away from the heart toward the brain. Example pump(s)) 306 may include any suitable catheter-based turbine pump.

Figure 4:
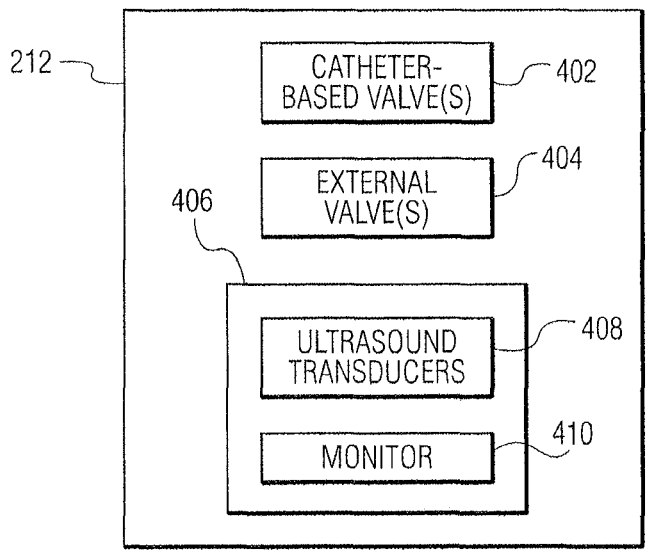
FIG. 4 is a functional block diagram of an exemplary valving system of the CPR device shown in FIG. 2, according to an embodiment of the present invention.

Referring next to FIG. 4, a functional block diagram of valving system 212 is shown. Valving system 212 may include one or more of catheter-based valve(s) 402, external valve(s) 404 and virtual valves 406. As discussed above, during CPR, blood is pumped by changing the pressure within the thorax with chest compressions. In this case, the cardiac valves are of little use. However, the presence of properly directioned elements (such as one-way physical valves or virtual valves) of valving system 212 positioned at the entrances and/or exits of the central vasculature may eliminate the sloshing observed during CPR.

The elements of valving system 212 may be mechanical and surgically placed using catheters (such as via catheter-based valves 402). The catheters may include, for example, balloon catheters or check valve catheters. The elements may also include external valves 404 capable of compressing a blood vessel until it collapses. The elements may also include virtual valves 406 (i.e., non-invasive valves) which use pressure pulses to counter the chest compression generated pressure pulse. Pressure pulses may be generated with ultrasound waves or with fluid filled catheters.

Although valving system 212 is described above with respect to hemodynamic instabilities, valving system 212 may also improve alternative techniques of blood flow generation. These techniques may include abdominal compression, periodic acceleration (pGz) (oscillating a prone body along its spinal axis), and alternatively raising of the legs or the head above the abdomen.

The elements of valving system 212 may be passive devices (i.e., check valves that open and close with changes in pressure and flow). The elements may also include active devices, which may be activated synchronously with chest compression mechanism 206 (FIG. 2).

In an exemplary embodiment, a single one-way valve may be positioned relative to the superior vena cava, without blocking the inferior vena cava. If a single valve is positioned relative to the inferior vena cava, the valve may cause the pressure to rise in the jugular veins during a chest compression, thereby decreasing forward blood flow through the brain. In contrast, a single valve positioned relative to the superior vena cava may increase forward blood flow through the brain, by isolating the jugular veins from the thoracic pressure increase caused by a chest compression.

In general, elements of valving system 212 may be positioned in (or externally coupled to) at least one of the inferior vena cava, the superior vena cava, the descending aorta, the jugular veins, the carotid arteries in the neck or the common carotid artery in the thorax, such that the elements may increase, but do not reduce, forward blood flow through the brain.

Catheter-based valve(s) 402 may include, for example, a passive one way valving system. Catheters(s) containing zero-pressure check valve(s) may be surgically implanted through common access points (e.g., femoral, brachial, neck). After implantation of the catheter based valve(s) 402, manual CPR may be initiated (by manual CPR performer 208 (FIG. 2)) or automatic CPR may be initiated by chest compressor mechanism 206.

According to an exemplary embodiment, catheter-based valves 402 of valving system 212 may be placed in the abdominal aorta and the carotid artery in the neck (to allow blood to leave the thorax, but not return), and catheter-based valves 402 may be placed in the jugular vein and the vena cava (to allow blood to enter the thorax, but not leave). Valves 402 may isolate the right and left sides of the vasculature from different phases of the chest compression induced thoracic pressure waveform. Valves 402 may also take advantage of a relatively large flow in the proper direction in each vessel, while mitigating the flow in the wrong direction.

Catheter-based valve(s) 402 may also include, for example, an active one way valving system which may be used in conjunction with chest compressor mechanism 206 (FIG. 2). Catheter based valves 402 may be positioned as set forth above, and may be timed to open and close synchronous with the chest compressions.

External valve(s) 404 may include a cervical collar that compresses the jugular and carotid vessels. The cervical collar may also be coupled to chest compressor mechanism 206 (FIG. 2), and may be timed to operate synchronous with chest compressions by chest compressor mechanism 206. External valve(s) 404 may also include a system for abdominal binding that may also be tightened/released in timing with the chest compressions.

Virtual valves 406 may include ultrasound transducers 408 and monitor 410, for non-invasive valving. Ultrasound transducers 408 are aimed at each other, and may emit at least two ultrasonic wave transmissions that are slightly out of phase. The interaction of the interfering ultrasonic waves may produce an ultrasonic standing wave in the bloodstream. This ultrasonic standing wave may interfere with blood motion, acting as a virtual valve. In an exemplary embodiment, ultrasound transducers 408 may be positioned, for example, so that standing waves may be established in the aorta, vena cava, jugular veins, and carotid arteries. According to another embodiment, the standing waves may be established synchronous with chest compressions by chest compressor mechanism 206 (FIG. 2). Monitor 410 may be used to visualize the blood vessels and to locate the desired blood vessels for ultrasound blocking.

Figure 5A:
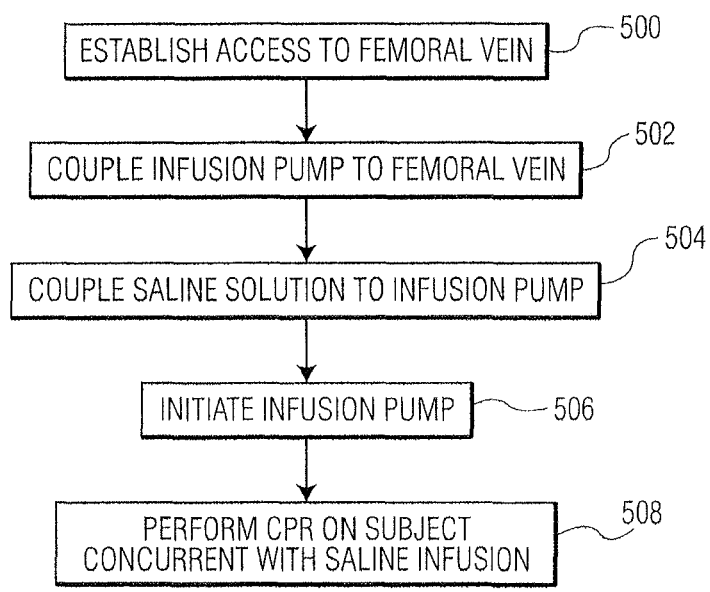
FIGS. 5A, 5B and 5C are flowcharts of exemplary methods for increasing forward blood flow via a pump system, according to embodiments of the present invention.
Figure 5B:
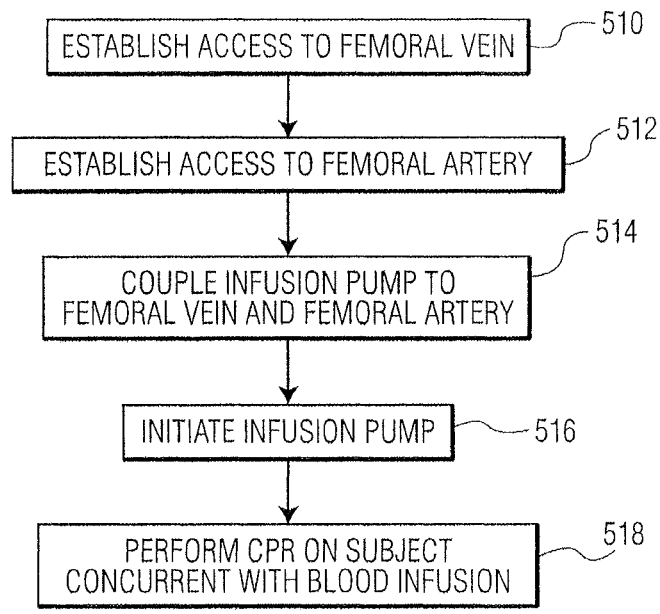
Figure 5C:
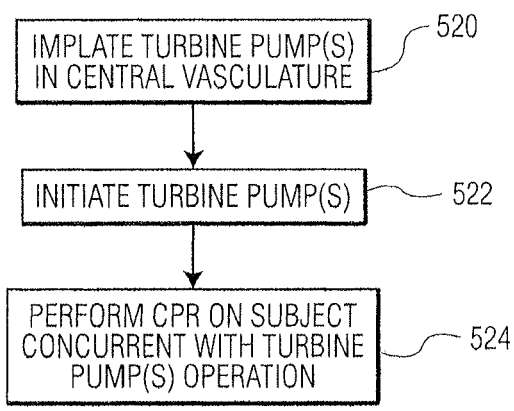

Referring next to FIGS. 5A-5C, flowcharts of exemplary methods for increasing forward blood flow via pump system 210 (FIG. 3) are shown. In particular, FIG. 5A is a flowchart illustrating an exemplary forward blood control method using fluid infusion system 302 (FIG. 3); FIG. 5B is a flowchart illustrating an exemplary forward blood control method using blood infusion system 304; and FIG. 5C is a flowchart illustrating an exemplary forward blood control method using catheter-based turbine pump(s) 306.

Referring to FIG. 5A, at step 500, access to the femoral vein is established, for example via femoral vein access device 308. At step 502, an infusion pump is coupled to the femoral vein, for example, infusion pump 310 may be coupled to the femoral vein via femoral vein access device 308. At step 504, a saline solution is coupled to the infusion pump. For example, saline solution 312 may be provided to infusion pump 310, as shown in FIG. 3.

At step 506, the infusion pump may be initiated, for example, by controller 204 (FIG. 2). At step 508, CPR may be performed on a subject concurrently with saline infusion, for example, by manual CPR performer 208 (FIG. 2) or by chest compressor mechanism 206, while infusion pump 310 is in operation. The CPR may be performed as directed by American Heart Association (AHA) guidelines.

Referring to FIG. 5B, at step 510, access to the femoral vein is established, for example via femoral vein access device 308. At step 512, access to the femoral artery is established, for example via femoral artery access device 314. At step 514, an infusion pump is coupled to output fluid to the femoral vein and to receive fluid from the femoral artery. For example, infusion pump 310 may be coupled to the femoral vein and the femoral artery via respective femoral vein access device 308 and femoral artery access device 314.

At step 516, the infusion pump may be initiated, for example, by controller 204 (FIG. 2). At step 518, CPR may be performed on a subject concurrently with blood infusion from the artery to the vein, for example, by manual CPR performer 208 (FIG. 2) or by chest compressor mechanism 206, while infusion pump 310 is in operation.

Referring to FIG. 5C, at step 520, at least one turbine pump may be positioned within the central vasculature, for example, at least one catheter-based turbine pump 306 may be positioned at one or more of the entrances or exits of the central vasculature. At step 522, the at least one turbine pump may be initiated, for example, by controller 204 (FIG. 2). At step 524, CPR may be performed on a subject concurrently with operation by turbine pump(s) 306, for example, by manual CPR performer 208 (FIG. 2) or by chest compressor mechanism 206.

Figure 6:
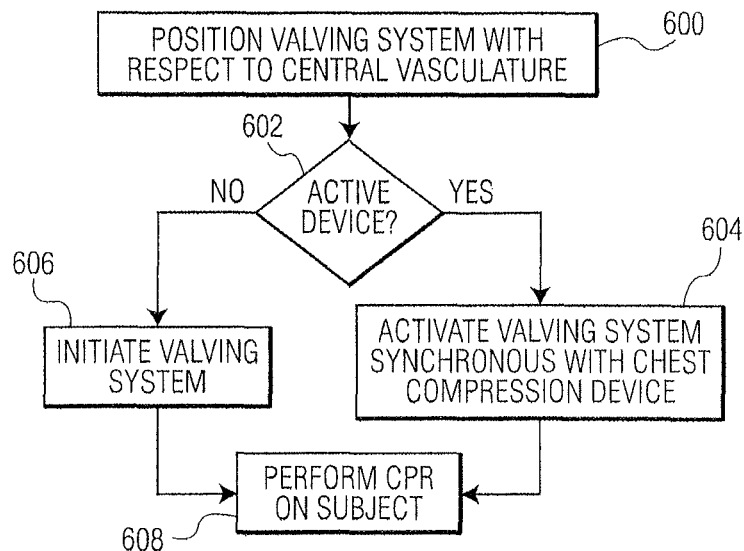
FIG. 6 is a flowchart of an exemplary method for increasing forward blood flow via a valving system, according to an embodiment of the present invention.

Referring next to FIG. 6, a flowchart of an exemplary method for increasing forward blood flow via valving system 212 (FIG. 4) is shown. At step 600, valving system is positioned with respect to the central vasculature. For example, at least one catheter-based valve 402 may be mechanical and surgically positioned in a desired blood vessel. According to another embodiment, at least one external valve 404 may be externally coupled to a desired blood vessel. According to a further embodiment, at least one pair of ultrasound transducers 408 may be positioned at a desired location, via monitor 410.

At step 602, it is determined whether valving system 212 includes an active device, for example, by controller 204 (FIG. 2). If an active device is included, step 602 proceeds to step 604.

At step 604, the valving system is activated synchronously with a chest compressor mechanism, e.g., valving system 212 is activated synchronously with chest compressor mechanism 206 via controller 204 shown in FIG. 2. For example, at least one of catheter-based valve(s) 402, external valve(s) 404 or virtual valve(s) 406 are activated. For manual CPR (for example, performed by manual CPR performer 208 (FIG. 2)), a pressure transducer may be used to detect chest compression and to control activation of elements of valving system 212. As another example related to manual CPR, an open loop timer may control activation of elements of valving system 212 with chest compression. Step 604 proceeds to step 608. At step 608, CPR is performed on a subject, for example, by chest compressor mechanism 206 (FIG. 2).

If it is determined, at step 602, that an active device is not included (i.e., valving system 212 includes a passive device), step 602 proceeds to step 606.

At step 606, the valving system is initiated. For example, at least one of catheter-based valve(s) 402, external valve(s) 404 or virtual valve(s) 406 are activated. Step 606 proceeds to step 608. At step 608, CPR is performed on a subject, for example, by chest compressor mechanism 206 (FIG. 2) or by manual CPR performer 208.

Figure 7A:
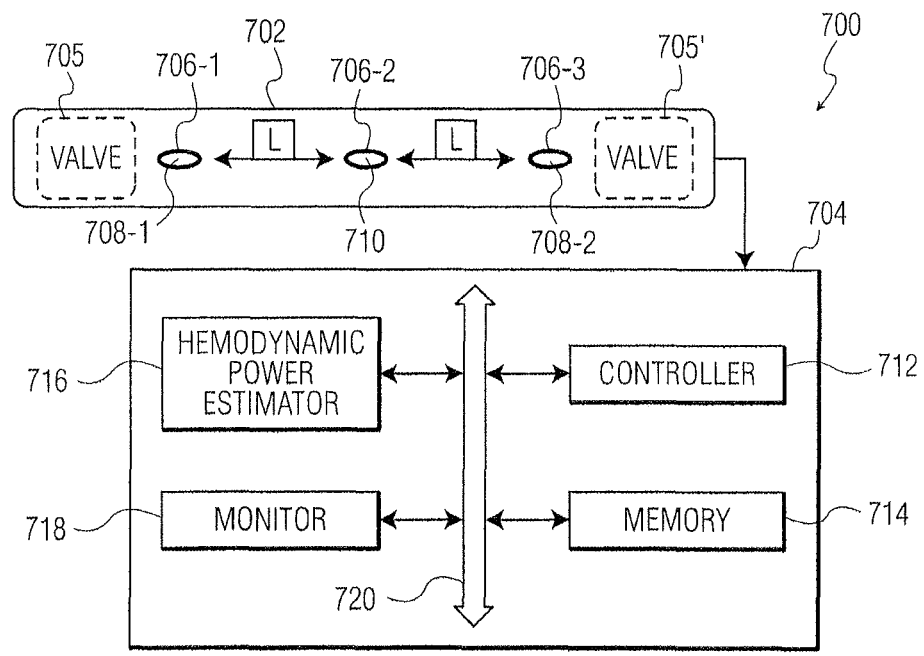
FIG. 7A is a functional block diagram of an exemplary hemodynamic power monitoring system, according to an embodiment of the present invention.

Referring next to FIG. 7A, a functional block diagram is shown of exemplary hemodynamic power monitoring system 700 (also referred to herein as system 700). System 700 may include power catheter 702 coupled to power estimation system 704. Power catheter 702 (in combination with power estimation system 704) may be used to monitor hemodynamic power in a blood vessel. A change in hemodynamic power may also be monitored by power catheter 702.

In general, power catheter 702 may include a measurement device configured to determine blood flow and blood pressure at a position within a blood vessel. FIG. 7A is described below for a specific embodiment including at least two pressure transducers 708, where the blood flow is determined using a pressure gradient technique. It is understood that the transducers 708 (and optional transducer 710) represent an example embodiment of a measurement device. Other sensors and/or techniques may be used to determine the blood flow and blood pressure in power catheter 702.

Although the pressure gradient technique is described further below, it is understood that power catheter 702 may also measure blood flow by other techniques, including, but not limited to, Doppler shift, measurement by a bristle flow meter, anemometry, thermodilution, the pitot technique, or measurement by an electromagnetic flowmeter.

Referring to the specific embodiment shown in FIG. 7A, power catheter 702 may monitor pressure and a change in pressure in a blood vessel. Power estimation system 704 may estimate the blood flow from the change in pressure. Power estimation system 704 may also determine the hemodynamic power by multiplying the pressure (from power catheter 702) by the estimated blood flow.

Cardiovascular function is generally defined by two distinct components, a potential energy component (pressure) and a kinetic energy component (flow). Conventional clinical monitoring typically ignores the kinetic energy component in favor of the potential energy component. It is known, however, from fluid dynamics that power may be determined by multiplying the volumetric flow rate with the pressure in real time. In mechanical systems, for example, pump efficiency curves are typically provided as a function of pump power. Therefore, it may be appreciated that monitoring cardiovascular power may provide an improved measure of cardiac function. The hemodynamic power may also provide an improved measure of the efficiency of chest compression (CPR).

Power catheter 702 may be configured to provide both a pressure measurement and a flow measurement. According to an exemplary embodiment, power catheter 702 may include two or three side-facing pressure ports 706-1, 706-2 and 706-3. Pressure ports 706 may be evenly spaced. In an exemplary embodiment, a distance (2L) between first port 706-1 and third port 706-3 is between about 2 and 4 cm. Transducers 708-1 and 708-2 may be positioned in respective ports 706-1 and 706-3. A further optional transducer 710 may be positioned in port 706-2.

In addition, the power catheter 702 may optionally include a valve 705 or 705' (both shown in phantom) that may be used, as described above with reference to FIGS. 2, 4 and 6. The valves 705 and 705' may be active valves, such as balloon catheters or passive valves such as check valves. In this combined catheter, the valve 705 is on one side of the pressure transducers 708. As shown in FIG. 7A, the valve 705 is on the left side of the catheter while the valve 705' is on the right side of the catheter. The combined catheter is used both to monitor and to control blood flow. The valve 705 is desirably placed on the side of the pressure transducers 708 that is near to the thorax. Thus, if the combined catheter is placed in the abdominal aorta, the valve 705 is desirably above the pressure transducers 708 (i.e. toward the thorax). When the combined catheter is inserted in the carotid artery, however, the valve 705 is desirably placed below the pressure transducers 708 (i.e. toward the thorax).

Figure 7B:
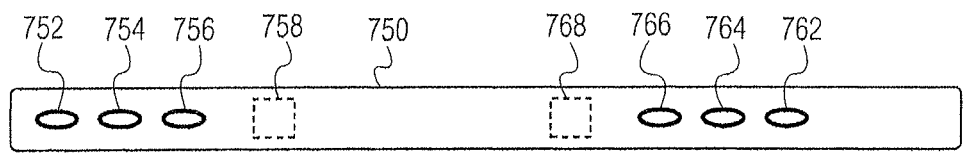
FIG. 7B is a block diagram of an alternative hemodynamic power monitoring catheter that may be used with the system shown in FIG. 7A.

FIG. 7B is a block diagram of an alternative power catheter 750 that includes two power sensors, each including two or three side facing pressure ports, 752, 754, 756, 762, 764 and 766 and corresponding sensors (not separately shown). The pressure ports are arranged in first and second groups. The first group, including pressure ports 752, 754 and 756 is separated from the second group including ports 762, 764 and 766 by a distance sufficient to place them on opposite sides of the thorax when inserted into the body through an artery such as the abdominal aorta or a vein such as the inferior vena cava. The first group of pressure ports is associated with an optional valve 758 and the second group is associated with an optional valve 768. Each of the groups of pressure ports, sensors and optional valve shown in FIG. 7B operates in the same way as the pressure ports 706-1, 706-2, and 706-3, sensors 708-1, 708-2 and 710 and valve 705, shown in FIG. 7A.

Pressures measured from transducers 708-1 and 708-2 and the corresponding pressure transducers in each of the groups of pressure ports of the power catheter 750 may be used to estimate the blood flow. In particular, a change in pressure (i.e., a pressure drop) between transducers 708-1 and 708-2 may be used to estimate the blood flow. A pressure from further transducer 710 may be used to measure the average pressure along a segment of power catheter 702. Alternatively, the pressure measured from transducer 708-1 or transducer 708-2 may provide this average pressure value.

Power estimation system 704 may receive the change in pressure (from transducers 708-1 and 708-2) and the pressure (from further transducer 710) and may determine the hemodynamic power. Power estimation system 704 may include controller 712, memory 714, hemodynamic power estimator 716 and monitor 718, which may be coupled together by data and control bus 720. When used with power catheter 750, the hemodynamic power estimator 716 may be configured to receive signals from the pressure transducers in the first set of pressure ports 752, 754 and 756 as well as signals from the pressure transducers in the second set of pressure ports, 762, 764 and 766. These signals may be multiplexed into a single hemodynamic power estimator 716 or processed in parallel by two hemodynamic power estimators (not shown).

Hemodynamic power estimator 716 (also referred to herein as estimator 716) may receive the change in pressure (from transducers 708-1 and 708-2) and, optionally, a pressure measurement (from further transducer 710) via controller 712, and may estimate the blood flow and the hemodynamic power.

According to an exemplary embodiment, estimator 716 may use the pressure gradient technique to estimate blood flow. For example, if two pressure transducers 708-1 and 708-2 are separated by a known distance (I) (i.e., distance 2L), the flow may be related to the pressure drop across the two transducers. Equation (1) relates flow to pressure as:

$$\Delta P(t) = \left(\frac{8\eta l}{\pi r^4}\right)Q(t) + \left(\frac{\rho l}{\pi r^2}\right)\frac{dQ(t)}{dt} \qquad (1)$$

where ΔP is the pressure drop, η is the blood viscosity, r is the radius of the blood vessel, ρ is the blood density, t is time, and Q(t) is the volumetric flow rate as a function of time. Estimator 716 may solve equation (1) for Q(t), provided that the radius of the blood vessel and the blood density are known. The pressure gradient technique may be useful as providing a directionality measurement during chest compression generated blood flow.

Given the estimated blood flow, estimator 716 may determine the hemodynamic power from equation (2) as:

$$\text{Power}(t) = P(t) \ast Q(t) \qquad (2)$$

In equation (2) the quantity P(t) may be determined from the pressure measured by further transducer 710. Thus, the hemodynamic power may be determined by multiplying the pressure measurement (from further transducer 710) with the flow estimate (from transducers 708-1, 708-2) in real time. Additionally average values can be calculated by using mean pressures and flows averaged over one chest compression or heart beat. Other calculations known in the art, such as root mean squared power, Fourier analysis, wavelet analysis, and trend tracking can be applied to this measurement.

As shown in equation (1), information regarding the diameter of the blood vessel and the density and the viscosity of the blood is also used to estimate the blood flow. The density and viscosity of the blood, for example, may be sampled and measured using power catheter 702. These measurements may be performed in real time or periodically. The diameter of the blood vessel, for example, may be estimated by inflating a balloon (some distance from pressure ports 706 that is integral to power catheter 702, but separate from the pressure measurements) and observing stoppage of the flow. Knowledge of the balloon geometry and inflated volume may allow for reasonable estimates of the vessel diameter. Rapid removal and return of blood volume near pressure ports 706 through an additional port (not shown) may also be used to estimate the diameter of the blood vessel.

It may be appreciated that the most accurate measurements may be provided by power catheter 702 that has the capacity to prescribe, or measure, the vessel diameter and measure the blood density and viscosity.

The hemodynamic power determined by estimator 716 may be displayed on monitor 718. When the power catheter 750 is used, separate hemodynamic power estimates may be displayed for the power sensors in each of the two groups of power ports. Memory 714 may also store at least one of the change in pressure (e.g. from transducers 708-1 and 708-2), the pressure (e.g. from optional further transducer 710), the estimated blood flow or flows (from estimator 718), the blood vessel diameter(s), blood properties (e.g., density and/or viscosity) or the hemodynamic power (from estimator 716) for one or more measurement times and/or from the sensors in the two groups of pressure ports if power catheter 750 is used. Memory 714 may include, a magnetic disk, flash memory, a database or essentially any local or remote device capable of storing data. Although not shown, power estimation system 704 may be coupled to a device in a remote location (such as via a global network).

Controller 712 may be coupled to one or more of memory 714, hemodynamic power estimator 716 and monitor 718, to control operation and/or adjustment of memory 714, hemodynamic power estimator 716 or monitor 718 during the hemodynamic power monitoring. Controller 712 may include, for example, a logic circuit, a digital signal processor or a microprocessor.

Figure 8A:
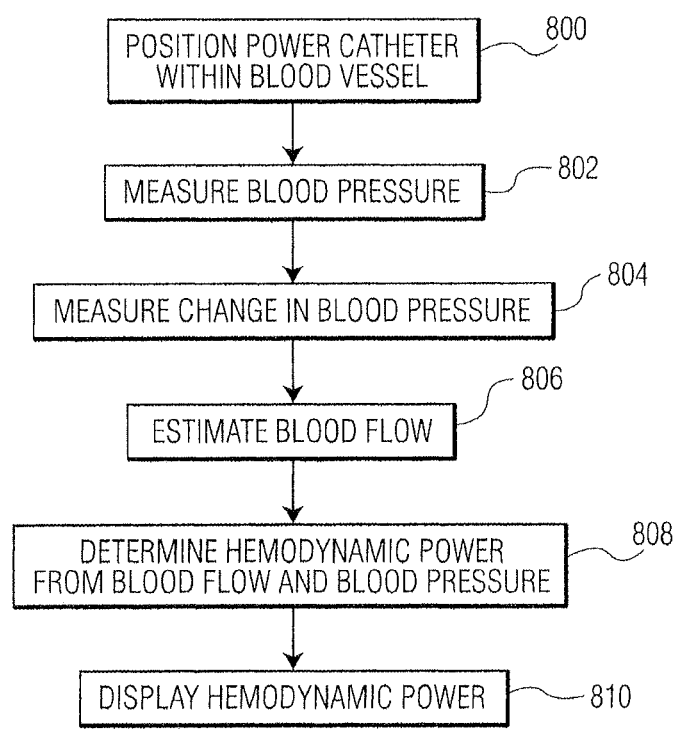
FIG. 8A is a flowchart of an exemplary method for monitoring hemodynamic power, according to an embodiment of the present invention.

Referring next to FIG. 8A, a flowchart of an exemplary method for monitoring hemodynamic power is shown. At step 800, a power catheter (e.g., power catheter 702) may be positioned in a blood vessel. At step 802, the blood pressure in the blood vessel is measured, for example, by transducer 710 of power catheter 702 shown in FIG. 7A or by one of the transducers 754 or 764 of FIG. 7B. At step 804, a change in the blood pressure may be measured, for example by transducers 708-1, 708-2 of power catheter 702 shown in FIG. 7A or by transducers 752, 758, 762 or 768 shown in FIG. 7B.

At step 806, the blood flow is estimated, for example, by estimator 716 (FIG. 7) from the change in the blood pressure (step 804) (such as via equation (1)). At step 808, the hemodynamic power may be determined (such as via equation (2)), for example, by estimator 716 (FIG. 7A) from the estimated blood flow (step 806) and the measured blood pressure (step 802). At step 810, the blood pressure may be displayed on a monitor, for example, by monitor 718 (FIG. 7A).

Figure 8B:
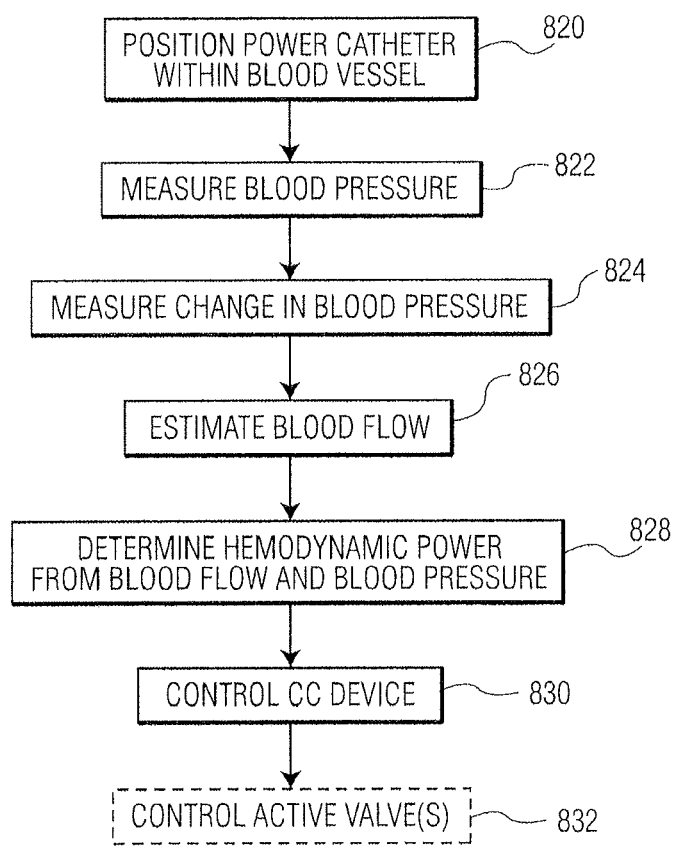
FIG. 8B is a flowchart of an exemplary method for controlling a chest compression device and optionally a valve using the hemodynamic power monitoring system shown in FIG. 7.

FIG. 8B is a flowchart diagram illustrating how the power catheter may be used in conjunction with a chest compression device and an active valve. Steps 820-828 of FIG. 8B are the same as steps 800-808 of FIG. 8A and are not described in detail. In step 830, the hemodynamic power estimate calculated by the apparatus shown in FIG. 7A using the power catheter 702 or the power catheter 750 is used to control the chest compression device. As described below with reference to FIGS. 9A-E, 10A and 10B, variations in the waveform applied to the chest compression device can affect the blood flow produced by the chest compressions. Several parameters of the waveform may be adjusted these include: the duty cycle (percentage of compression time versus non-compression time), frequency (number of compressions per minute), compression depth (amount of deflection of the sternum), release time (how quickly the compression is released), and compression time (how quickly the sternum is compressed).

In performing CPR, the goal is to increase forward blood flow. As described below, the inventors have determined that hemodynamic power is strongly correlated with blood flow. In step 830, the hemodynamic power estimate on one or both sides of the thorax may be used to adjust one or more of the duty cycle, frequency, compression depth and release time in a manner that increases hemodynamic power, and thus, blood flow. When the chest compression device is first attached to the patient, initial values for the parameters may be estimated based on the weight, height and age of the patient. In one control mode, the parameters may then be individually incremented and decremented to determine which adjustment improves blood flow. Alternatively, in another control mode, heuristics may be used to adjust a parameter in a way that is known to increase blood flow. For example, as described below with reference to FIGS. 10A and 10B, decreasing the release time tends to increase blood flow. Thus, if the release time is not near its minimum value, it may be decreased at step 830 to increase blood flow.

The hemodynamic power estimator shown in FIG. 7A using the power catheter 702 or the power catheter 750 may also be used to control active valves as shown in step 832 of FIG. 8B. As described above, these may be invasive valves, such as balloon catheters or non-invasive valves such as the abdominal binding and the cervical collar. If the valves are invasive valves, they may be included in power measurement catheter, as described above with reference to FIGS. 7A and 7B. The power estimates may be used to control the phasing of the valve openings with respect to the chest compressions generated by the chest compression device. This phasing ensures that the valve are open when the flow is positive and closed when the flow is negative, to reduce sloshing. The valves may be controlled at step 832 by monitoring the hemodynamic energy when the valves are held open and then adjusting the timing of the valves so that they are open only when the blood flow is in the preferred direction.

The present invention is illustrated by reference to several examples. The examples are included to more clearly demonstrate the overall nature of the invention. These examples are exemplary, and not restrictive of the invention.

Example 1

The existence of a blood volume shift during resuscitation has been a hypothetical explanation of the observed reduction in chest compression (CC) efficacy as a function of time. However, central blood flows, and therefore volumes, have not been thoroughly investigated during prolonged CPR.

CPR hemodynamics in nine domestic swine (about 30 kg) were studied using standard physiological monitoring. Flow and pressure sensors were placed on the abdominal aorta (AA) and the inferior vena cava (IVC) slightly inferior to the kidneys. Ventricular fibrillation (VF) was electrically induced. Mechanical CC were started after ten minutes of untreated VF and continued for 54 minutes.

Hemodynamic data indicate that study animals may be separated into two groups depending on the direction of net IVC flow at the end of the experiment. IVC and AA flows were significantly different between animals with net forward IVC flow (IVCpos) and net negative IVC flow (IVCneg). IVCneg animals had higher forward AA flows. At the end of the resuscitation, IVCneg animals were adding blood volume to the tissue below the flow probes, and IVCpos animals were removing blood volume from the tissue below the flow probes. The hemodynamic data results are shown in Table 1.

TABLE 1

Hemodynamic Data Results

| | IVC flow [ml/min] | | Abdominal Aorta flow [ml/min] | |
|---|---|---|---|---|
| | Initial | End | Initial | End |
| IVCneg (n = 4) | 24 ± 33.4 | −51.14 ± 22.4 | 68.1 ± 18.9 | 8.0 ± 2.0 |
| IVCpos (n = 5) | 67.8 ± 12.8 | 49.9 ± 13.9 | 76 ± 88 | −2.1 ± 1.8 |
| p-value | 0.22 | 0.005 | 0.87 | 0.006 |

Both the IVCneg and the IVCpos groups experienced significant volume shifts during the resuscitation, however, the volume shifts appear to be in opposite directions. The volume shifts between these reservoirs has a profound impact on the distribution of CC generated blood flow.

Example 2

Research has suggested that chest compression (CC) release velocity or waveform impacts CPR effectiveness.

CPR hemodynamics in eight domestic swine (about 30 kg) were studied using standard physiological monitoring. A flow probe was placed on the AA and a pressure catheter tip was located in a corresponding region. Ventricular fibrillation (VF) was electrically induced. Mechanical CC were started after ten minutes of untreated VF. CC release was adjusted so that sternal recoil lasted 100 ms, 200 ms, or 300 ms. CC were delivered over 54 min at a rate of 100 per minute and at a depth of 1.25 in. Transitions between waveforms occurred every 2 min and were randomized. Hemodynamic power was calculated as flow*pressure. A peak decay phase was identified during which the drop in power over time became exponential.

Peak decay in AA power started after approximately 12 minutes of CPR. Pairwise comparisons indicated a significant effect of CC waveform. Transitioning from 300 ms to 100 ms release time increased average AA power by 8.5±13.6% while the reverse transition caused a decrease of −14.1±14.1% (p<0.001). Transitioning from 200 to 300 ms release time had a similar negative effect on AA power (−8.7±8.4%) whereas comparisons between 100 ms and 200 ms release times showed no significant difference.

Thus, the inventors have determined that CC release velocity significantly alters abdominal aortic hemodynamic power during prolonged CPR. Faster release velocities were associated with preserved or improved power, whereas slower release velocities were associated with significant reductions in power.

Example 3

CPR hemodynamics in eight domestic swine (about 30 Kg) were studied using standard physiological monitoring. Flow probes were placed on the abdominal aorta, the inferior vena cava (IVC), the right renal artery and vein, the right common carotid and external jugular. Ventricular fibrillation (VF) was electrically induced. Mechanical CC were started after ten minutes of untreated VF. CC release was changed so that sternal recoil lasted 100 ms, 200 ms, or 300 ms. 54 min of CC were delivered at a rate of 100 per minute and at a depth of 1.25 in. Transitions between waveforms occurred every 2 min and were randomized.

Analyses of the recorded hydrodynamic power (power=flow*pressure) indicated that there was a significant difference in the amount of energy each CC waveform transferred to the blood in the IVC (100 ms=0.022±0.008, 200 ms=0.020±0.008, 300 ms=0.018±0.006 watts, p<0.001 for all comparisons between waveforms). This difference was observed throughout the duration of testing. No significant differences were found between the amounts of net forward flow generated by each CC waveform in any vessel. Significant to and fro blood flow (sloshing) was observed during all chest compressions, regardless of CC waveform.

Thus, the inventors have determined that CC release velocity does not have a significant effect on net forward flow during a chest compression, but does have a significant effect on the amount of hydrodynamic power transferred to the blood in the IVC.

Example 4

Figure 9A:
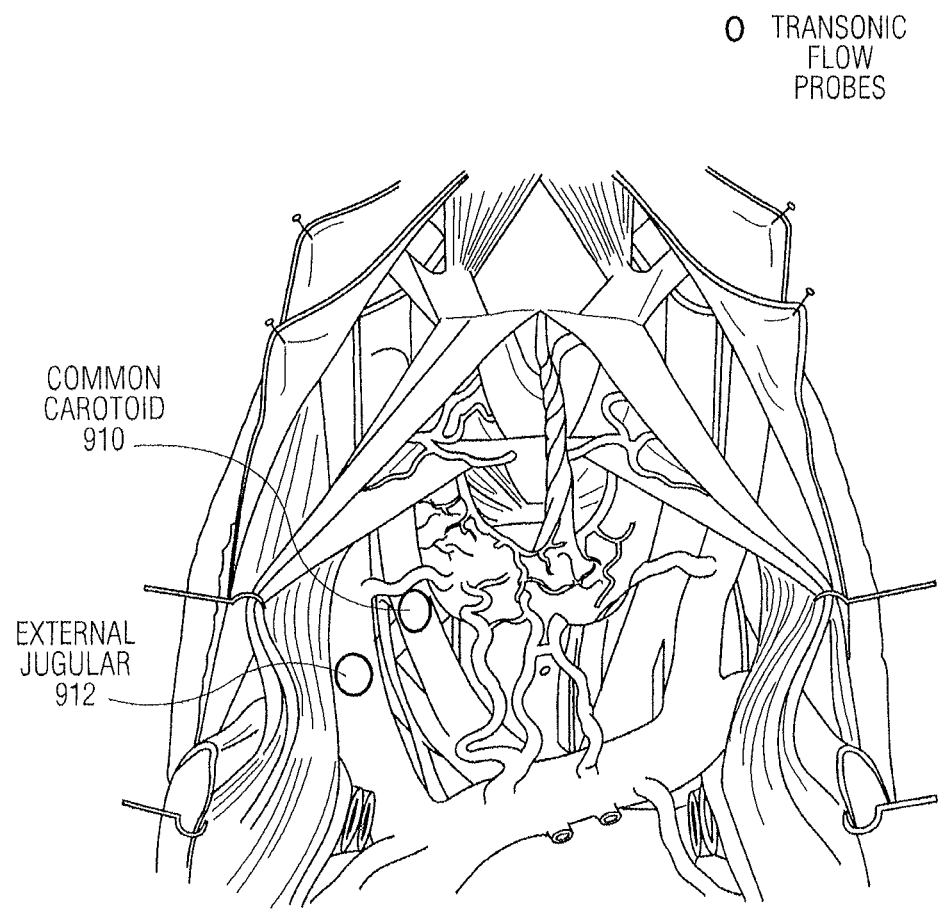
FIGS. 9A and 9B are anatomical drawings that are useful for describing the placement of sensors.
Figure 9B:
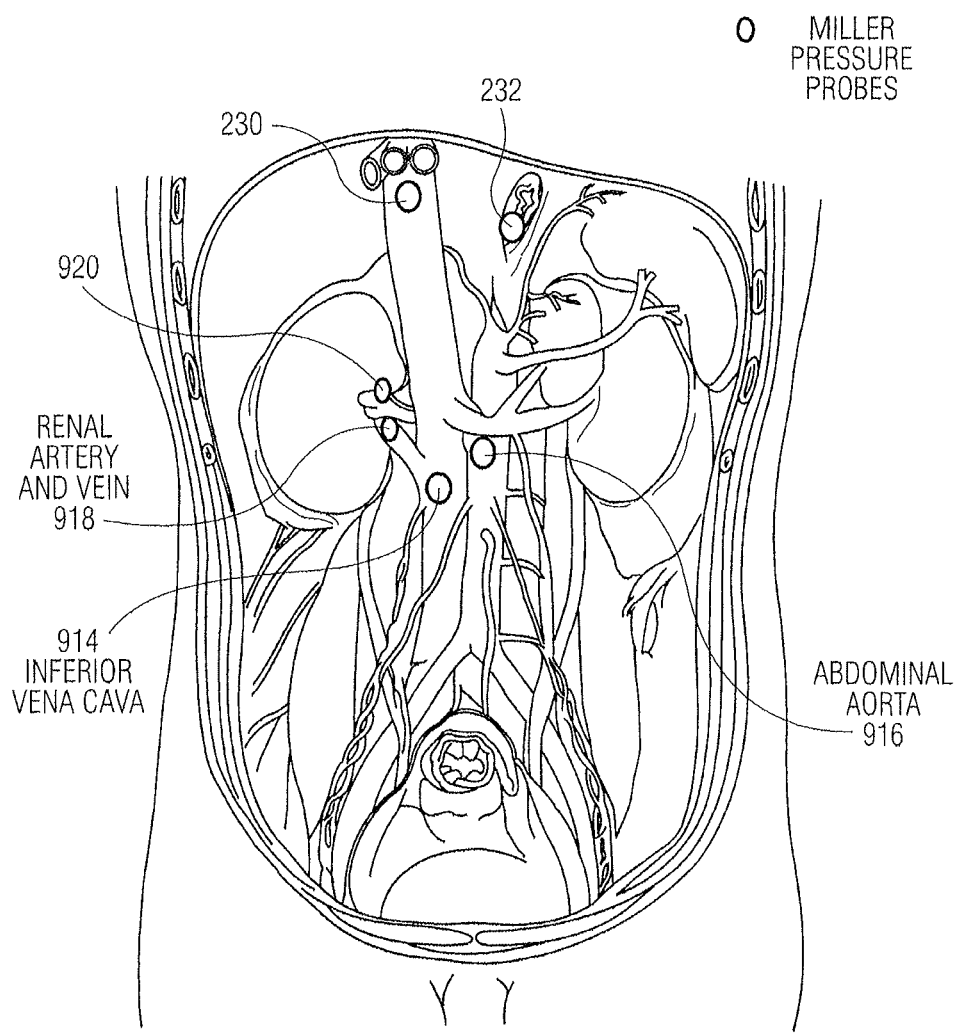

CPR hemodynamics in eight female domestic swine (~30 kg) were studied using standard physiological monitoring. Hemodynamic power was calculated by multiplying blood flow by blood pressure. As shown in FIGS. 9A and 9B, flow probes (e.g. Transonic flow probes) were placed in various vascular beds including a first probe 910 in the common carotid artery, a second probe 912 in the external jugular vein, a third probe 914 in the abdominal aorta, a fourth probe 916 in the inferior vena cava and fifth and sixth probes 918 and 920 in the renal artery and vein. In addition, as shown in FIG. 9A, pressure catheter tips (e.g. Millar pressure probes) 930 and 932 were placed in the aorta and right heart. Although separate pressure and flow sensors were used in this example, it is contemplated that a combined sensor, such as that described above with reference to FIG. 7 could be used in place of the pressure sensors. Furthermore, although pressure sensors were not placed in the common carotid artery, the external jugular vein, the abdominal aorta, the inferior vena cava and the renal artery and vein, a combined sensor inserted in any of these locations may provide equivalent measurements.

Figure 9C:
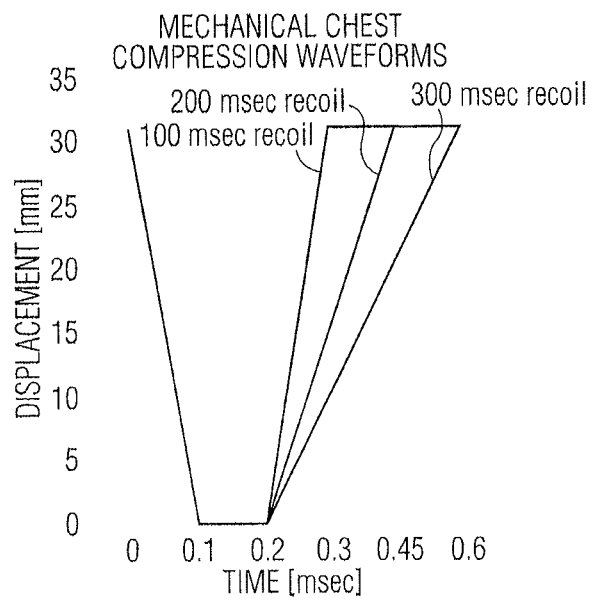
Figure 9D:
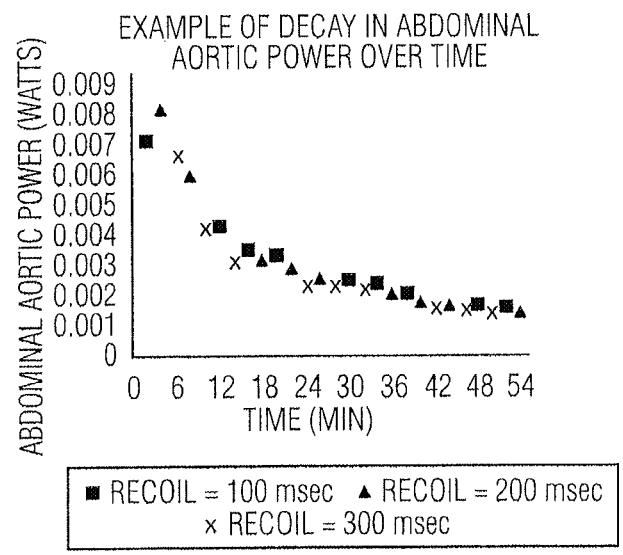

Next, ventricular fibrillation (VF) was electrically induced. Mechanical chest compressions were started after ten minutes of untreated VF. As shown in FIG. 9C, the release portion of the chest compression waveform was adjusted so that sternal recoil lasted 100 ms, 200 ms, or 300 ms. The chest compressions were delivered over 54 min at a rate of 100 per minute and at a depth of 1.25 inch with transitions between waveforms occurring every 2 min. FIG. 9D shows an example of the decay in abdominal aortic power over time for an individual animal with the square points representing the chest compression waveforms having a 100 ms recoil, the triangle points representing waveforms having a 200 ms recoil and the "x" points represent waveforms having a 300 ms recoil. As can be seen in this graph, there is a progressive exponential decline in abdominal aortic power during prolonged VF despite continuous chest compressions.

FIGS. 10A and 10B show the results of averaging the abdominal aortic power measurements over time and the carotid flow measurements over time for all of the animals in the group. A peak decay time at approximately 12 minutes of CPR was identified after which the drop in power over time became exponential. As shown, the power measurement in the common aorta has good correspondence to the flow measurement in the carotid artery. Thus, this power measurement may be used in place of a flow measurement to determine CPR efficacy.

Figure 9E:
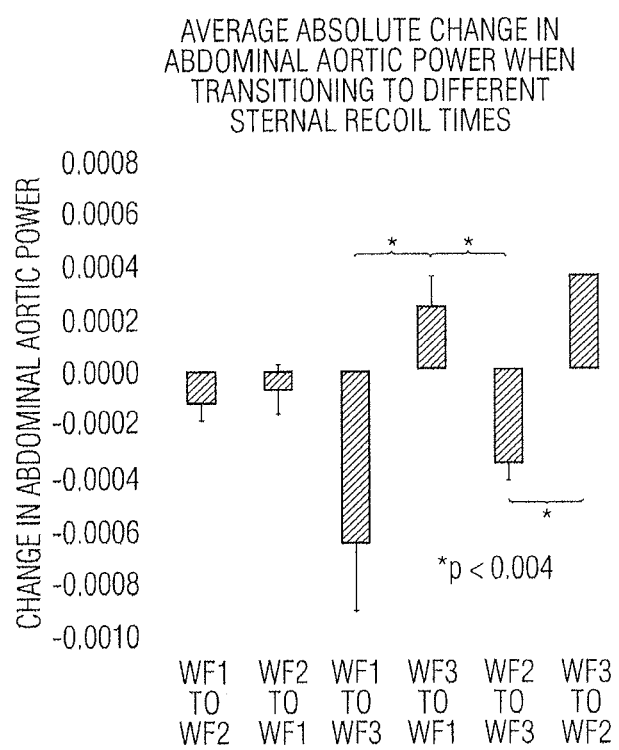

FIG. 9E shows the change in abdominal aortic power that occurs on switching among the waveforms. In this graph, waveform 1 (WF1) has a 100 ms recoil, WF2 has a 200 ms recoil and WF3 has a 300 ms recoil. Pairwise comparisons indicate a significant effect of chest compression waveform. Transitioning from 300 ms to 100 ms release time increased average abdominal aortic power by 8.5±13.6% while the reverse transition caused a decrease of −14.1±14.1% (p<0.001) Transitioning from 200 ms to 300 ms release time had a similar negative effect on abdominal aortic power (−8.7±8.4%). Comparisons between waveforms with release times of 100 ms and 200 ms show no significant difference.

As can be seen from FIGS. 9E, 10A and 10B, chest compression release velocity significantly alters abdominal aortic hemodynamic power during prolonged CPR. Faster release velocities were associated with preserved or improved power, whereas slower release velocities were associated with significant reductions in power.

Example 5

Animal research has suggested that inducing therapeutic hypothermia during the arrest period (e.g. during chest compressions) may provide more benefit than inducing hypothermia after return of spontaneous circulation. Hypothermia induction technologies can be divided into two classes: technologies that use volume infusions, and technologies that do not.

In an example method that uses volume infusion, 18 temperatures were monitored in 24 domestic swine (~30 Kg) during intra-arrest hypothermia induction with ongoing CPR. Mechanical chest compressions and hypothermia induction were started after ten minutes of untreated VF. Chest compressions were performed at a rate of 100 per minute and a depth of 1.25 inches for 60 minutes. The example included a control group in which no hypothermia induction techniques were used. The hypothermia induction techniques used on the remaining animals included: femoral vein cold saline infusion, femoral vein ice slurry infusion, carotid cold saline infusion, carotid ice slurry infusion, nasopharyngeal cooling, heat exchange catheter cooling and blanket cooling. The procedure was terminated after 60 minutes of chest compressions and cooling.

During the procedure, three Liters femoral vein (FV) infusions of cold saline and ice particulate slurry were administered using a pump at a rate of ~75 ml/min. This infusion significantly increased $EtCO_2$ during CPR at times 20-30 min ($EtCO_2$ FV=29.63 mmHg vs. $EtCO_2$=22.16 mmHg, p<0.05), 30-40 min ($EtCO_2$ FV=23.8 mmHg vs. $EtCO_2$=13.94 mmHg, p<0.05), and 40-50 min ($EtCO_2$ FV=20.07 mmHg vs. $EtCO_2$=10.69 mmHg, p<0.05), with a trend toward significance at 50-60 min ($EtCO_2$ FV=16.84 vs. $EtCO_2$=8.26, p=0.056). Carotid infusions of similar volumes at similar rates, however, did not improve $EtCO_2$ during prolonged CPR.

Thus, high volume femoral infusions administered during CPR significantly increased measured values of $EtCO_2$. This data supports the hypothesis that imposing a volume driven flow in the femoral vein during CPR improves venous return.

Figure 11A:
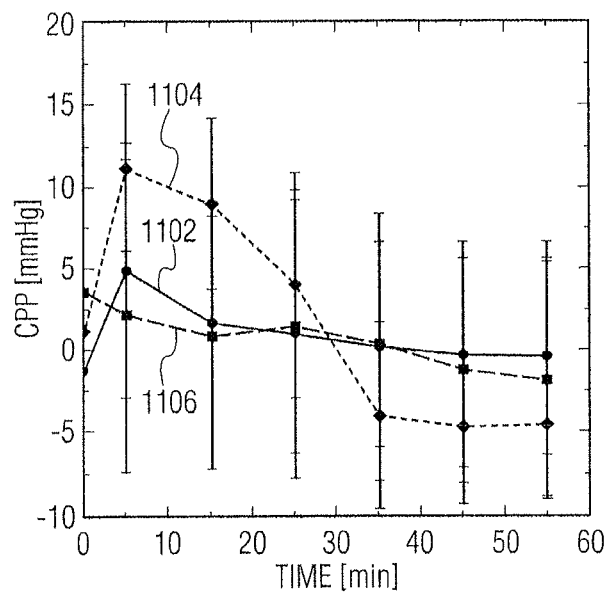
FIGS. 11A and 11B are graphs that are useful for describing effects of venous and arterial fluid infusion during CPR.
Figure 11B:
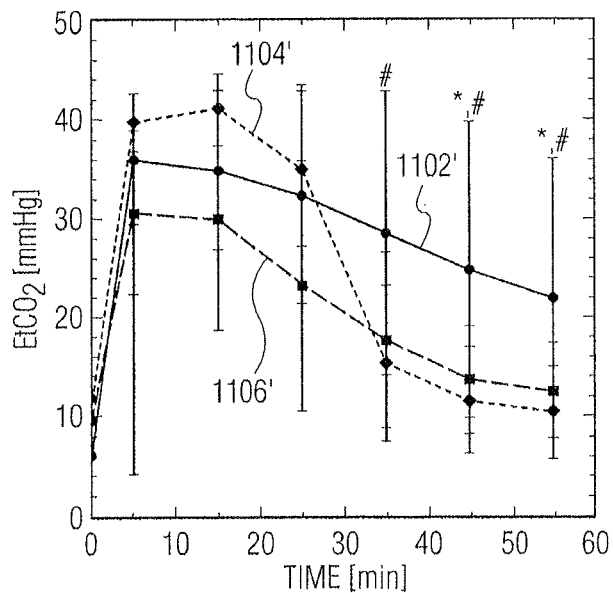

FIG. 11A is a graph of average coronary perfusion pressure (CPP) versus time. FIG. 11B is a graph of $EtCO_2$ versus time. In these graphs, the value reported at t=0 is the value right before initiation of chest compressions. Data for the volume cooling (VC) group are represented by curves 1102 and 1102' in FIGS. 11A and 11B, respectively. Data for the no volume cooling (NVC) group are represented by respective curves 1106 and 1106'. Data for the no cooling (NC) group are represented by the respective curves 1104 and 1104'. The asterisk (*) symbol represents statistical difference (P<0.05) between the VC and NC groups and the pound sign (#) represents statistical difference between the VC and NVC groups. FIG. 11A shows that the addition of fluid does not improve coronary perfusion. FIG. 11B illustrates that arterial and venous delivery of saline during CPR both improve venous return and EtCO2.

Although the invention is illustrated and described herein with reference to specific embodiments, the invention is not intended to be limited to the details shown. Rather, various modifications may be made in the details within the scope and range of equivalents of the claims and without departing from the invention.

What is claimed:

1. A blood flow enhancement device for use during administration of cardiopulmonary resuscitation (CPR) to a subject, comprising:
   (i) an active one-way valving system positioned within a first blood vessel of the subject, the active one-way valving system configured to reduce backward blood flow in the first blood vessel during the administration of CPR;
   (ii) a mechanical chest compression device for providing chest compressions to the subject during the administration of CPR, the mechanical chest compression device having a plurality of adjustable parameters comprising at least one of: chest compression frequency, chest compression duty cycle, chest compression depth, chest compression release time, and time to complete sternal compression; and
   (iii) a hemodynamic power measurement system including:
      a measurement device configured to be positioned in a second blood vessel of the subject, the measurement device configured to measure blood flow and blood pressure in the second blood vessel during the administration of CPR, and
      a power estimation system coupled to the measurement device, the power estimation system configured to determine a hemodynamic power based on the measured blood flow and the measured blood pressure during the administration of CPR,
   wherein the determined hemodynamic power is applied as an input to the mechanical chest compression device to adjust at least one of the adjustable parameters of the plurality of adjustable parameters to enhance the administration of CPR.

2. The blood flow enhancement device of claim 1, wherein the active one-way valving system is positioned in a superior vena cava of the subject.

3. The blood flow enhancement device of claim 1, wherein the first blood vessel includes at least one of a superior vena cava, an inferior vena cava, an aorta, a jugular vein or a carotid artery of the subject.

4. The blood flow enhancement device of claim 1, wherein the determined hemodynamic power is applied to the active one-way valving system to control timing of opening and closing of the at least one active one-way valving system.

5. A method of enhancing forward blood flow during cardiopulmonary resuscitation (CPR), the method comprising:
   positioning an active one-way valving system within a first blood vessel of the subject's central vasculature, the active one-way valving system configured to reduce blood flow in the first blood vessel;
   initiating the active one-way valving system during the CPR such that the active one-way valving system is configured to increase the forward blood flow generated during the CPR in the central vasculature without reducing the forward blood flow through a brain of the subject; and
   with
   (i) a mechanical chest compression device for providing chest compressions to the subject during the administration of CPR, the mechanical chest compression device having a plurality of adjustable parameters comprising at least one of: chest compression frequency, chest compression duty cycle, chest compression depth, chest compression release time, and time to complete sternal compression, and
   (ii) a hemodynamic power measurement system including:
      a measurement device configured to be positioned in a second blood vessel of a subject, the measurement device configured to measure blood flow and blood pressure in the second blood vessel during the administration of CPR; and
      a power estimation system coupled to the measurement device, the power estimation system configured to determine a hemodynamic power based on the measured blood flow and the measured blood pressure during the administration of CPR,
   determining with the power estimation system a hemodynamic power that is applied as an input to the mechanical chest compression device to adjust at least one of the adjustable parameters of the plurality of adjustable parameters to enhance the administration of CPR.

6. The method of claim 5, wherein the active one-way valving system is positioned in a superior vena cava of the subject.

7. The method of claim 5, wherein the first blood vessel includes at least one of a superior vena cava, an inferior vena cava, an aorta, a jugular vein or a carotid artery of the subject.

8. The blood flow enhancement device of claim 1, wherein the active one-way valving system is configured to be activated synchronously with a CPR chest compression to increase forward blood flow generated during the CPR in the central vasculature without reducing the forward blood flow through the brain of the subject.

9. The blood flow enhancement device of claim 1, wherein the determined hemodynamic power is applied as an input to the chest compression device to adjust at least the chest compression frequency and the chest compression depth of the chest compression device.

10. The method of claim 5, wherein the hemodynamic power is applied as an input to the chest compression device to adjust at least the chest compression frequency and the chest compression depth of the chest compression device.

* * * * *